United States Patent [19]

Wells et al.

[11] Patent Number: 4,752,448
[45] Date of Patent: Jun. 21, 1988

[54] DRUG ABUSE TEST PAPER

[75] Inventors: Henry J. Wells, Columbia; Robin L. Binder, Millersville, both of Md.

[73] Assignee: Keystone Diagnostics, Inc., Columbia, Md.

[21] Appl. No.: 943,539

[22] Filed: Dec. 17, 1986

Related U.S. Application Data

[63] Continuation-in-part of Ser. No. 810,099, Dec. 18, 1985, abandoned.

[51] Int. Cl.$^4$ .................. G01N 21/78; G01N 33/52; G01N 33/94
[52] U.S. Cl. .................................... 422/56; 422/57; 436/92; 436/96; 436/98; 436/111; 436/169; 436/901
[58] Field of Search ............... 422/56, 57, 58; 436/92, 436/96, 98, 111, 169, 901

[56] References Cited

U.S. PATENT DOCUMENTS

| | | | |
|---|---|---|---|
| 3,043,669 | 7/1962 | Charles | 422/56 |
| 3,552,925 | 1/1971 | Fetter | 422/56 X |
| 3,590,006 | 6/1971 | Page et al. | 436/162 |
| 3,832,134 | 8/1974 | Sohn | 436/92 X |
| 3,891,507 | 6/1975 | Breuer | 422/56 X |
| 3,912,655 | 10/1975 | Shukla et al. | 422/56 X |
| 3,914,174 | 10/1975 | Fuchs | 422/56 X |
| 3,915,639 | 10/1975 | Friedenberg | 422/56 X |
| 3,955,926 | 5/1976 | Fischer | 422/58 X |
| 3,963,421 | 6/1976 | Jones | 436/92 X |
| 4,652,529 | 3/1987 | Collins et al. | 436/92 |

FOREIGN PATENT DOCUMENTS 8402397  6/1984  PCT Int'l Appl. .

Primary Examiner—Barry S. Richman
Assistant Examiner—Robert J. Hill, Jr.
Attorney, Agent, or Firm—Pennie & Edmonds

[57] ABSTRACT

A diagnostic test paper detects abuse-type drugs in a test specimen of a biological fluid. A particular method of making the diagnostic test paper includes impregnating a bibulous carrier material with the dry residue of a reagent reactive to abuse-type drugs. A particular method is used for screening a biological fluid to determine the presence of abuse-type drugs therein. A test specimen applying area is located on the bibulous carrier material adjacent one side of a concentrated reagent zone having a first color. A particular method of application and a specific syringe device is used to apply a test specimen that has been prepared under very precise conditions. The test specimen moves from the particular applying area into the concentrated reagent zone to produce the specific results of detecting the presence of abuse-type drugs therein. A novel solvent composition is used to prepare the test specimen applied to the bibulous carrier material of the invention.

7 Claims, 1 Drawing Sheet

DRUG ABUSE TEST PAPER

This application is a continuation-in-part of application Ser. No. 810,099, filed Dec. 18, 1985, now abandoned.

FIELD OF THE INVENTION

This invention relates to a procedure for detecting the presence of abuse-type drugs in biological fluids. More particularly, the invention is directed to a procedure comprising a simplified screening method which provides rapid qualitative results for use in determining the need for additional or confirmatory testing.

BACKGROUND OF THE INVENTION

There are several well known qualitative laboratory procedures for identifying drugs of abuse. These include Thin-Layered Chromatography (TLC), the Enzyme Multiplied Immuno-chemical Test (EMIT), Radioimmunoassay (RIA) and Gas-Liquid Chromatography (GLC). Each of these well known procedures require skilled technicians and relatively sophisticated equipment. Consequently, the testing procedure is necessarily expensive.

With the ever increasing rise in the use of abuse-type drugs, the need for detecting and identifying those drugs and their metabolites is becoming more important. With this need, many more tests are required to monitor the use of abuse-type drugs.

Thin layer chromatography screening procedures for detecting drugs in urine require the careful preparation of a test specimen and then a skillful application of that test specimen to a plate placed into a developing chamber. Once the plate is removed from the chamber and dried, it is sprayed with visualization reagents. Location and color of spots are compared with those of known standards. Qualitative judgments are made as to the presence of various drugs in the unknown sample. The procedure is tedious, time consuming and requires skilled personnel to interpret the results.

The EMIT procedure is a semi-quantitative immunoassay for drugs of abuse in biological fluids. The laboratory test requires trained technicians to perform and the equipment necessarily costs several thousands of dollars. The RIA procedure is a sensitive and quantitative laboratory procedure for detecting drugs of abuse. The various immunochemicals are labeled with radioactive compounds and require special care in their use and disposal. A license is required from the government to use this laboratory procedure because of the presence of radioactive materials. The GLC procedure can provide the highest degree of accuracy in drug analysis. However, the necessary equipment is expensive and the procedure is complicated. Consequently, highly trained personnel are required for its use.

The visualization reagents used in thin-layer chromatography are well known and their use is explained in U.S. Pat. No. 3,590,006. A particular method of handling the chemical visualization reagents for the TLC procedure is found in the U.S. Pat. No. 3,912,655. Here dry strips of paper impregnated with fixed amounts of the visualization reagent are prepared as a storage medium for the reagent to be used in the thin-layer chromatography procedures. Both of these disclosures are directed to producing a drug abuse test paper designed to replace the thin-layer chromatography procedure. Thus, both are designed to produce both a qualitative and quantitative analysis of abuse-type drugs in a biological fluid.

The U.S. Pat. No. 3,955,926 discloses a test process suitable for identifying narcotics in solid form. A sample of the material which is suspected to be a narcotic is subjected to a solvent for that particular narcotic. An absorbent, impregnated paper containing at least one component of a color reagent in dry form is then subjected to the solvent. This particular prior art test is not applicable to the detection of the presence of an abuse-type drug in a biological fluid such as urine.

A drug abuse test indicator device and a method of making same is disclosed in the international publication WO No. 84/02397. Here the matrix of a bibulous material is impregnated with a dry staining agent in precise amounts which are prepared in accordance with unique procedures whereby pH insensitivity and unique color change sensitivities to test fluids are obtained. This disclosure is said to be an improvement over the procedure disclosed in U.S. Pat. No. 3,915,639 which discloses the use of coatings on a carrier body requiring the use of an ion exchange resin, a staining agent and a color intensifier-stabilizer material. Each of these earlier disclosures make use of the visualization reagents commonly used in the thin-layer chromatography procedures. Both of these disclosures are directed to producing a drug abuse test paper designed to replace the thin-layer chromatography procedure. Thus, both are designed to produce both a qualitative and quantitative analysis of abuse-type drugs in a biological fluid.

Major difficulties exist in the production of the drug abuse test papers designed to replace the thin-layer chromatography procedure. These difficulties are associated with the necessity to use extremely controlled environments in the production of the papers. Thus, large production requirements for such papers while achieving commercial consistency has been a major problem. However, these papers represent the first successful attempts to detect the presence of abuse-type drugs by having visualization reagents present in a carrier matrix material change color within that matrix upon the direct application of a test specimen.

In view of the difficulties associated with known procedures and drug abuse test papers, the diagnostic test paper of the present invention has been developed for use as a confirmatory test for the presence of abuse drugs. The present system developed in accordance with this invention is not intended for monitoring therapeutic levels nor as a basis for any therapeutic treatment based on test results. The invention of this disclosure is designed as a simplified screening method providing rapid qualitative results for use in determining the need for additional or confirmatory testing. The basic idea is to screen the numerous samples of biological fluids collected at collection centers for drugs of abuse and their screening programs and determine which ones are a positive. Only those which show a positive result are then sent on the laboratory for further testing.

The diagnostic test procedure and its equipment is readily understood by persons who are unskilled in chemical laboratory procedures. That is, the primary users of the test will be the staff of the various collection centers such as clinics specifically set up for screening programs, methadone treatment centers and the like.

The procedure of the present invention is a qualitative test based on color producing visualization reagents used in thin-layer and paper chromatography. In general, TLC visualization reagents are used to react with materials of interest to produce an area that is visually distinct from the background due to unreacted reagent. The invention of this system does not attempt the separation and identification of individual components. Rather, the system is a method of screening biological fluids to determine the aggregate presence of materials which react with the visualization reagent impregnated in the test paper. Through the use of unskilled personnel, very inexpensive equipment and the rapid determination of negative results, the screening procedure of the present invention provides an extremely important advance in the drug abuse detection technology. That is, thousands of tests will no longer have to be conducted using the more sophisticated TLC, EMIT, RIA and GLC procedures.

SUMMARY OF THE INVENTION

The invention as disclosed and described herein includes a diagnostic test paper, a method of making the test paper, a method of using the test paper, a syringe assembly and a particular solvent composition useful in preparing a test specimen of a biological fluid.

The diagnostic test paper comprises a bibulous carrier material impregnated with a dry residue of a visualization reagent reactive to abuse-type drugs. The carrier material includes a test specimen applying area and a concentrated color producing visualization reagent zone. The test specimen applying area is located adjacent to one side of the concentrated reagent zone and has a first color. The visualization reagent is present in the concentrated reagent zone in an amount sufficient to change color in the carrier material when contacted by abuse-type drugs introduced into the carrier material via a test specimen.

A specific embodiment of the diagnostic test paper includes the use of a solution of potassium iodide and hexachloroplatinate in which the iodoplatinate visualization reagent is formed. The reagents may be impregnated into the paper by dipping a bibulous carrier material therein or applied to the carrier material in a dropwise fashion. Either type of reagent paper will function in the system of this invention with differing degrees of sensitivity. The dipped carrier material results in a lower loading of the reagent. The use of drops on discrete areas of a sheet of bibulous carrier material produces a higher concentration of the visualization reagent. In the specific example of the present procedure, the test paper is used to perform the method of screening urine specimens for the presence of narcotic substances of abuse. That is, the visualization reagent in the specific embodiment of this invention is reactive to the following abuse-type drugs and/or their metabolites opiates, cocaine including free-base cocaine, phencyclidine (PCP) and phenothiazines, heroin, codeine, morphine, methadone, amphetamine and benzodiazepine.

Once the visualization reagent impregnates the carrier material, it is then necessary to form the test specimen applying area. A wash solution is applied over the location where the visualization reagent has been impregnated. This wash solution causes amounts of the reactive reagent to move into a concentrated visualization reagent zone from the area in which the wash solution has been applied. This area becomes the test specimen applying area for the subsequent application of a test specimen of a biological fluid. Thus, the concentrated reagent zone defines the outer peripheral profile of the test specimen applying area. Where the wash solution is applied to a specific location via drops, the concentrated reagent zone comprises an annular perimeter zone around the test specimen applying area. Once the paper has dried after application of the wash solution, it is ready for the test procedure involving the preparation of a test specimen and its application directly to the test specimen applying area.

A specific embodiment of the diagnostic test paper provides a bibulous carrier material having a test specimen applying area, a concentrated reagent zone and an initial, reagent concentration region. The test specimen applying area is located on one side of the concentrated reagent zone. The initial, reagent concentration region is located on the other side of the concentrated reagent zone opposite said one side thereof. The concentration of the impregnated reagent within the concentrated reagent zone is greater than the concentration of the impregnated reagent within the initial, reagent concentration region. The concentration of the impregnated reagent within the test specimen applying area is less than the concentration of the impregnated reagent within the initial, reagent concentration region.

A specific embodiment of the test paper is directed to the drop application of a mixture of potassium iodide and iodoplatinate to form a reddish-brown spot on the surface of a bibulous carrier material such as a paper strip. The matrix of the paper strip has the capacity to hold a liquid test specimen for a time sufficient to react any substance contained therein which might be reactive with the iodoplatinate reagent. A wash solution such as a deionized, distilled water is applied to the reddish-brown spot to form a discrete, washed area therein. The bibulous material is dried after the iodoplatinate reagent is placed onto the sheet and before the wash solution is applied. The drying of the impregnated bibulous carrier material is sufficient to preclude irregular diffusing of the visualization reagent residue into the matrix of the bibulous material. Thus, the reddish brown spot is produced having a washed center portion with a grayish annular ring surrounding the washed, test specimen applying area. Upon drying, the diagnostic test paper may be used with two different tests. The urine specimen may be applied to the test specimen applying area with either (1) no pretreatment or (2) having first been subjected to a cleanup procedure. This will depend upon the particular situation in which the diagnostic test paper is being used. If the location for urine specimens deals with a high percentage of negative urines, there is no necessity to use the cleanup procedure of the present invention on each individual sample. When the test paper indicates a positive test on the untreated urine specimen, it is then subjected to the cleanup procedure of the present invention and tested again. The cleanup procedure of the invention is designed to eliminate any false positives which might turn up in the raw urine specimen.

The cleanup procedure according to the present invention involves the use of a syringe assembly comprising a syringe canister including a plunger element and a packing material disposed therein. The plunger element is slidably disposed to successively pull into and discharge out materials being subjected to the chemically adsorbent material constituting the packing. The purpose of this cleanup procedure is to eliminate interfering or extraneous materials which may cause a false positive. The specific embodiment of this invention includes use of a reverse phase liquid chromatography material. The urine specimen is successively pulled into contact with the packing column and discharged out the same inlet. A wash solution is then drawn into the syringe to eliminate the interfering substances. The solvent solution in the present case is an acetone containing toluenesulfonic acid which eludes any narcotic substances bound to the packing. The organic solvent with the narcotic substances dissolved therein are then applied directly to the test specimen applying area of the diagnostic test paper. After a brief drying period, water is then applied to this test specimen applying area and any narcotic substances will cause the formation of a blue-gray ring to form around the test specimen applying area.

BRIEF DESCRIPTION OF THE DRAWINGS

Other objects of this invention will appear in the following description and claims, reference being made to the accompanying drawings forming a part of the specification wherein like reference characters designate corresponding parts in the several views.

DETAILED DESCRIPTION

Figure 1:
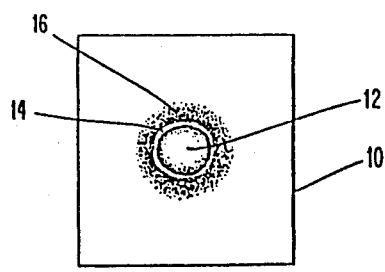
FIG. 1 is a plan view of a diagnostic test paper made in accordance with this invention.

This invention provides a means for detecting the presence of drugs of abuse and/or their metabolites rapidly and accurately. Such drugs of abuse capable of being screened include cocaine (all forms) including "crack" (a free-base form of cocaine), morphine, heroin, PCP ("angel dust" or phencyclidine), amphetamines, methadone, codeine, other opiates, benzodiazepines and related molecules and phenothiazines. Specifically with regard to heroin and codeine, this test detects the presence of their metabolite, morphine.

The bibulous carrier material 10 used in this invention is impregnated with a dry residue of visualization reagent. Bibulous carrier materials which have been used successfully include Whatman No. 3 paper, Kim-Wipe, Schleicher & Schuell filter and electrophoresis paper products such as SS-598, 2043a and 593, glass fiber and non-woven fabric such as bonded polyester or bonded nylon. The carrier material used throughout the various embodiments of this invention is SS-598.

The reagent material used in this specific embodiment includes a mixture of potassium iodide (KI) and hexachloro-platinate. Potassium iodide is present in the molar range of from about 1.0M to about 0.55M with the hexachloroplatinate present in the molar range of about 0.002M to about 0.024M. The specific reagent in this particular instance included 0.488M of potassium iodide and 0.019M of hexachloroplatinate.

Upon preparation of the reagent, it is necessary to maintain an excess of potassium iodide so that the maximum amount of iodoplatinate will be disposed in the matrices of the test papers 10, 20, 22 and 25 of the several embodiments. The constituents of the visualization reagent solution before applying to the carrier material are formed in a 0.05N hydrochloric acid.

A drop of the reagent solution as prepared above is placed upon the strip or sheet of carrier material. Each drop is in the amount of from about 20 to 40 microliters. In the embodiment shown in FIGS. 1-4, a drop is about 20 microliters and forms a reddish-brown spot upon application to the carrier materials 10, 20, 22 and 25 as shown. A more definitive range for the amount of initial reagent formulation added to the various carrier materials is from about 20 to 25 microliters.

After the initial drop has been dried and the reddish-brown spot has formed, a test specimen applying area is made in the center of the reagent spot. An amount of wash solution in the range of from about 4 to about 10 microliters is applied to the center of the brown spot. A more definitive range for the wash solution is from about 8 to about 10 microliters. The wash solution in this particular embodiment is the deionized, distilled water. The water is applied via a pipette to allow the water to move by capillary action radially from the point of application to the brown spot. The water washes the reagents into a concentrated band or annular ring at the edge of the test specimen applying area. The annular concentrated reagent zone defines the outer peripheral profile of the test specimen applying area.

In FIG. 1, the test specimen applying area 12 is surrounded by the inner annular ring 14 defining the concentrated visualization reagent zone and an outer annular ring 16 defining an initial, reagent concentration region. Each test paper starts with configuration as shown in FIG. 1. The concentration of the impregnated reagent within the concentrated reagent zone 14 is greater than the concentration of the impregnated reagent within the initial, reagent concentration region 16. The concentration of the impregnated reagent within the test specimen applying area 12 is less than the concentration of the impregnated reagent within the initial, reagent concentration 16.

Figure 2:
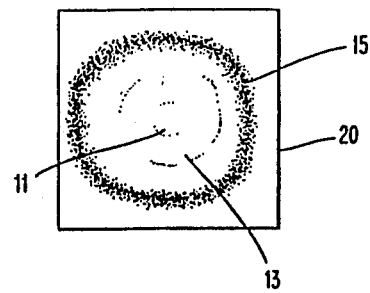
FIG. 2 is a test paper as shown in FIG. 1 after an untreated urine specimen has been applied thereon showing a negative result.

The carrier 20 shown in FIG. 2 depicts a diagnostic test paper having been subjected to an untreated urine specimen applied to the test specimen applying area 11. An extremely faint annular zone 13 having substantially no color indicates that the specimen is negative. The initial, reagent zone 15 surrounds the entire area that has been washed outwardly by the as is application of the urine specimen.

Figure 3:
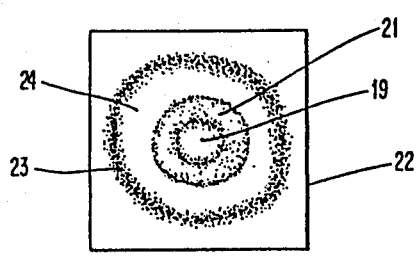
FIG. 3 is a top plan view of a test paper as shown in FIG. 1 after a test specimen having a positive result showing presence of a narcotic abuse-type drug.

The carrier material 22 as shown in FIG. 3 began with a test paper that looked like the one shown in FIG. 1. In this embodiment, a urine specimen was treated with the cleanup procedure of the present invention to prepare a test specimen which is added to the test specimen applying area 19. The definitive ring 21 was formed upon the application of the test specimen indicating a positive response. The cleanup procedure used with the embodiment shown in FIG. 3 included the use of acetone as a solvent composition followed by a final water washing step to form the area 24 between the darkened annular ring 21 and the initial, reagent concentration zone 23.

Figure 4:
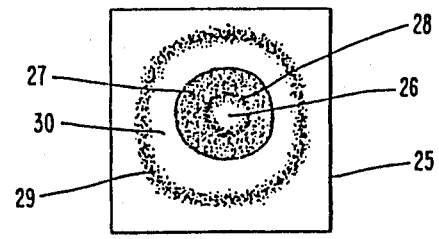
FIG. 4 is a top plan view of a test paper of FIG. 1 after applying a test specimen showing another positive result indicating presence of an abuse-type drug in the test specimen applied thereto.

The embodiment as shown in FIG. 4 indicates a carrier material 25 having a test specimen applying area 26, a definitive blue-grey ring 27 having a darker inner ring 28. The initial concentration outer ring 29 has a washed area 30 next adjacent to it. The spiked sample in this embodiment included cocaine and produced a much darker ring 27 than the ring 21 as shown in the embodiment of FIG. 3. Interfering and extraneous materials were first removed from the urine specimen according to the cleanup procedure of the invention to prepare the test specimen applied to the center of the diagnostic test paper which initially looked like the test paper as shown in FIG. 1.

The purpose of the cleanup procedure is to eliminate the effects of materials such as nicotine, and commercial materials such as Elavil, Sinequan and Dalmane/Atavan. These latter prescription drugs may cause false positive results. Other over-the-counter preparations containing ephedrine or pseudoephedrine are also desired to be eliminated because they may give false positive reactions.

A standard syringe having a syringe canister with a slidably disposed plunger element therein is used to draw material into it to contact a packing material. In this cleanup preparation for testing for the presence of narcotic substances, a reverse phase liquid chromatographic packing is used.

The isolation procedure of the present invention provides a short column in the syringe canister containing a non-polar adsorbent packing material under conditions which cause the drugs and other interfering materials to be retained by the adsorbent. The plunger is operated to successively pull into and out of the column a measured amount of the biological fluid; namely, urine. The column material may be selected from any one of the group of extraction columns for urine drug abuse screening procedures. This includes a Tox Elut extraction column which is a product of Analytichem International, Baker-10 SPE, a product of J.T. Baker Chemicals and Extrelut QE, a product of EM Sciences.

Such well known columns are normally used in expensive vacuum equipment which operate to pass the materials through the column in one direction only. It was found to be totally unexpected that such a procedure could even produce the kind of excellent chromatographic results as have been achieved in accordance with the present invention.

The various components including the interfering and extraneous materials along with any abuse-type drug present in the urine is retained by the adsorption column. An acidic rinse solution is then drawn into and discharged from the syringe canister to satisfactorily eliminate any of the interfering and extraneous materials retained on the column. At the same time, the acidic rinse solution leaves any abuse-type drug which may have been present in the urine retained by the column.

Following the rinsing step, a solvent solution made in accordance with this invention is passed over the chemically adsorbent material to form the test specimen having any abuse-type drug retained on the adsorbent material dissolved in said solvent solution. The solvent solution made in accordance with this invention is an acetone having a pH in the range of less than 2.0. A specific embodiment has acid added to acetone to produce a pH of about 1.6. The specific acid used with the acetone is toluenesulfonic acid in the range of from about 0.25% to about 1.0%. The specific embodiment used in the preparation of test specimens for the embodiment shown in FIGS. 3 and 4 had an acid concentration of 0.5% weight per volume.

The specific packing was a phenyl reverse phase packing which may be used in various types of solvents to remove the abuse-type drugs retained thereby. Various other acids may be used with acetone but the most significant results were unexpectedly obtained with the toluenesulfonic acid.

The rinse solution was a hydrochloric acid solution having a pH of about 2.3. The rinse solution may comprise a hydrochloric or nitric or other inorganic acid solution having a pH in the range of from about 0.5 to about 4.0 and may include an indicator compound such as thymol blue.

Upon pulling in the acetone solvent solution as prepared above, the test specimen is then slowly discharged out of the syringe canister until a yellow (or pink if indicator present) colored fluid appears at the tip of the syringe. This is particularly associated with the specific embodiment of this particular invention. The syringe tip is then touched to the white test specimen blank area 12 allowing the acidic solvent to migrate from the center of the paper across the inner annular ring 14. Enough elution solvent is applied to the center area 12 to wet the area inside the outermost brown reagent ring 16. The solvent is then allowed to evaporate. This may take up to two minutes.

Once dried, using a pipette or an eye dropper, four to five drops of wash water are added to the center of the test area 12. Excess reagent will be washed away and a gray, inner ring will always appear. If it is a negative specimen, the gray area will be very faint. However, if narcotic substances are present, a distint blue-gray color will form between the area wetted by the elution solvent and the outer ring 16. The embodiments of FIGS. 3 and 4 show a positive specimen. The test ring is negative if the area outside the inner gray ring is diffuse and pale gray in color and there is no well defined blue outer edge. See the embodiment of FIG. 2.

Samples yielding a positive result by the method of the present application should always be tested using a different technique for confirmation. Any ambiguous or uncertain results should also be sent out for further testing with a different technique such as those discussed hereinabove. The purpose of the present invention is simply to eliminate a host of tests which normally would have to be conducted using the extremely expensive laboratory procedures which are already available and well known as discussed hereinabove. A positive test is indicative of the presence of an abuse-type drug in a person from whom the biological fluid sample was taken. Since many abuse-type drugs are metabolized rapidly, a positive test may also indicate the presence of that metabolite and the exposure of that person to the abuse-type drug from which the metabolite was derived.

The amount of water used after the application of the acetone acid solution is from about 60 to 120 microliters of water.

For appropriate operation of the procedure of this invention, a minimum of 1.5 milliliter of urine is required. Fresh urine specimens or those which have been refrigerated up to two weeks may be used. Specimens remaining refrigerated for longer than a two week period or unrefrigerated may cause false positive reactions due to decomposition of components in the urine. The preservatives methyl or ethyl paraben do not interfere with the test. The urine solution must be in a pH range of 2.0 to 7.0. This is when used in conjunction with the reverse phase liquid chromatographic packing. It is necessary to have the urine specimen with this particular pH range to retain both the drugs and the interfering substances on the packing. The elution solvent solution unexpectedly found to produce the best results was an acetone having toluenesulfonic acid present in the range of from 0.25 to 1.0% weight per volume. However, any strong acid is believed to be workable in this system including the use of hydrochloric, sulfuric, phosphoric and nitric acids.

The syringe-column-combination may be regenerated after each sample has been cleaned up. It has been unexpectedly found that a single column packing can be used for at least 50 tests. It must be carefully flushed after each use. The flushing procedure includes drawing eluting solution into the barrel or syringe canister. The plunger is then removed and the liquid contents poured into a waste container. The replaced plunger is then used to draw water into the column. The plunger is again removed and the water poured into the waste container. The second water wash step is repeated. Then the column is packed with water ready for further use. The water is removed from the column before another urine sample is drawn therein for the next procedure.

It has been unexpectedly found that the procedure according to this invention is substantially equivalent to currently marketed thin-layer and paper chromatographic products. The consistency of the present screening method falls in the range of 90 to 94% accuracy when compared to tests carried out by laboratory procedures such as thin-layer chromatography.

The following examples according to this invention are given hereafter. These examples are meant to be illustrative and not to be considered as limiting the scope of the invention.

EXAMPLE 1

This example was carried out according to the procedure in accordance with this invention and as set forth below. This example describes tests in biological samples for the presence of the drug cocaine in its free-base form (otherwise known to the public as "crack"). Crack is made from the powdered cocaine-hydrochloride salt by dissolving this salt in warm water followed by the addition of baking soda or ammonia. The free-base (crack) is insoluble in water and precipitates out of solution. Crack is ingested by inhalation of the vapors produced by heating. These vapors enter the bloodstream very rapidly through the mucous membranes in the lungs and nasal cavity.

The test paper utilized in this example was prepared according to the procedures set forth above and comprised a paper impregnated with a mixture of potassium iodide and potassium iodoplatinate in a concentrated color producing visualization zone and including a test specimen applying area. The syringe comprised a syringe canister, slideable plunger and absorbent packing material (reverse phase liquid chromatographic packing) disposed within the canister. The elution (or solvent) solution comprised acetone containing toluenesulfonic acid. The wash solution was distilled water. The rinse solution (pH 2.3) comprised a dilute nitric acid solution with potassium nitrate and thymol blue. Each of three beakers was filled with one solution comprising either the rinse solution, elution solution or water.

Eight (8) urine samples were received from a reliable source. These samples were taken after the subjects had used "crack", marijuana, beer and wine.

The subjects were all males under the age of thirty (30). One had taken the crack, marijuana and alcohol 32-36 hours prior to collection of the urine samples. The other 7 consumed the crack and other substances 5-9 hours prior to collection of the urine samples. The samples were refrigerated and frozen until tested.

Three to four ml of rinse, wash or elution solution was required for each test. The tip of the syringe column was placed in the Elution Solution (acidic acetone) and the plunger was pulled up to draw the Elution Solution to an indicated fill line above the packing. The tip of the syringe column was kept well below the liquid level to keep from drawing air into the syringe. The plunger was depressed, expelling the liquid into a waste container.

The specimen number or code on the test paper was recorded. The tip of the syringe column was placed into the urine and the plunger was pulled up to draw the specimen to the indicated fill line on the syringe. The urine was discharged into the waste container by pushing down on the plunger. A yellow-brown band of material was seen at the bottom of the column packing. The fluid was drawn from the Rinse Solution beaker into the barrel of the syringe column to the indicated fill line. A red or pink band appeared at the bottom of the packing. The liquid was discharged into the waste container by pushing down on the plunger.

The acidic rinse steps were repeated trying to keep air out of the syringe. All of the liquid was not discharged. The column packing was kept wet for the next step, by stopping discharging when the liquid level was just above the column packing. The Elution Solution was slowly drawn up so that the red band moved about ½ way up the column packing. The plunger was slowly depressed, discarding drops until pink fluid appeared in the tip. There was a pause between the drops, allowing the next two drops to fall onto the white area in the center of the test paper. The pause allowed the first of these drops to spread through the paper before applying the second drop. The applied solution was allowed to dry. This took about a minute or two.

After the Elution Solution had dried on the test paper, the test was then completed by, with the pipette, applying at least four to six drops of water, slowly, to the center of the test area. The red color washed away. It was washed well clear of the area previously wet by the two drops of Elution Solution. When crack was present, a distinct blue-gray color formed over the entire area wet by the drops of Elution Solution. This area was clearly darker than the surrounding area. The results are indicated in Table I below.

The numbers assigned to each urine were KDI identification numbers. The specimens were received totally unidentified as to which were ingested 32-36 hours or 5-9 hours prior to collection of the urine.

TABLE I

| KDI # | Test Result for Presence or Exposure to Crack |
|-------|----------------------------------------------|
| 4907  | positive |
| 4908  | positive |
| 4909  | strong positive |
| 4910  | positive |
| 4911  | positive |
| 4912  | strong positive |
| 4913  | strong positive |
| 4914  | positive |

It is indicated from the results set forth in Table I that all of the above urine samples tested positive, in varying degrees, to the presence of crack. The test results would not be altered by the presence of marijuana or alcohol or their metabolites which may be excreted in the urine.

If test had been negative the area wet by the Elution Solution would not develop a distinct color. A negative test may have a distinct, thin ring at the outer edge of the Elution Solution zone. This ring's presence is not important can be ignored. (A small inner gray ring always appears). However, none of the above samples produced a negative result.

EXAMPLE 2

A total of 331 urine specimens shown by thin layer chromatography (TLC) to be either drug free or to contain morphine, cocaine, PCP or amphetamines were tested using the procedure set forth in Example 1. Using a paired-results evaluation with TLC, the inventive procedure herein identified as positive 176 (90.7%) of 194 samples determined positive by TLC and as negative 121 (88.3%) of 137 samples determined negative by TLC.

While the drug abuse test paper and methods for detecting drugs of abuse have been shown and described in detail, it is obvious that this invention is not to be considered as limited to the exact form disclosed, and that changes in detail and construction may be made therein within the scope of the invention without departing from the spirit thereof.

Having thus set forth and disclosed the nature of this invention, what is claimed is:

1. A diagnostic test paper for detecting abuse-type drugs in a test specimen of a biological fluid, said test paper consisting essentially of:

a dry bibulous carrier material impregnated with a visualization reagent reactive with abuse-type drugs, said carrier material including a test specimen applying area, a concentrated reagent zone, and an initial reagent concentration region, said test specimen applying area being located adjacent one side of the concentrated reagent zone, said initial reagent concentration region being located adjacent a side of the concentrated reagent zone opposite the test specimen applying area, the concentration of the visualization reagent within the concentrated reagent zone being greater than the concentration of the visualization reagent within the initial reagent concentration region, the concentration of the visualization reagent within the test specimen applying area being less than the concentration of the visualization reagent within the initial reagent concentration region, and the visualization reagent being present in the concentrated reagent zone in an amount sufficient to change color in the carrier material when contacted with abuse-type drugs introduced into said carrier material via a test specimen.

2. The test paper as defined in claim 1, wherein the visualization reagent is such that it is reactive with cocaine, including free-base cocaine, phencyclidine, benzodiazepine, phenothiazines, amphetamine, methadone, codeine, heroin, and morphine.

3. The test paper as defined in claim 1, wherein the visualization reagent is such that it is also reactive with a metabolite of an abuse-type drug.

4. The test paper as defined in claim 1, wherein the visualization reagent is a mixture of potassium iodide and potassium iodoplatinate.

5. The test paper as defined in claim 1, wherein the visualization reagent is potassium hexaiodoplatinate.

6. The test paper as defined in claim 1, wherein the bibulous carrier material is such that is has a capacity to hold a liquid test specimen for a time sufficient to react any abuse-type drugs therein with the visualization reagent.

7. The test paper as defined in claim 1, wherein the visualization reagent is impregnated in the bibulous carrier material in a substantially round, discrete spot having a center area defining the test specimen applying area surrouned by an inner annular ring defining the concentrated reagent zone and an outer annular ring defining the initial reagent concentration region.

* * * * *